United States Patent [19]

Kushner et al.

[11] 3,999,945
[45] Dec. 28, 1976

[54] LIQUID ANALYSIS SYSTEM

[75] Inventors: Jack Kushner, Lindenhurst; Henry G. Zwirblis, Nesconset, both of N.Y.

[73] Assignee: Delta Scientific Corporation, Lindenhurst, N.Y.

[22] Filed: Aug. 30, 1974

[21] Appl. No.: 501,875

[52] U.S. Cl. .................. 23/253 R; 73/421 R; 209/3; 209/156; 222/133; 259/4 R
[51] Int. Cl.² ................ G01N 1/12; G01N 31/00; B03D 3/00
[58] Field of Search .............. 23/253 R, 259, 292; 259/4; 209/156, 162; 222/133 US

[56] References Cited
UNITED STATES PATENTS

| | | | |
|---|---|---|---|
| 2,422,656 | 6/1947 | Carter, Jr. | 259/4 |
| 2,534,656 | 12/1950 | Bond | 23/253 R X |
| 2,977,199 | 3/1961 | Quittner | 23/253 R X |
| 2,980,512 | 4/1961 | Petersen | 23/253 R |
| 3,102,789 | 9/1963 | Pirsh et al. | 23/253 R X |
| 3,104,153 | 9/1963 | Ekegren | 259/4 X |
| 3,219,208 | 11/1965 | Hadley et al. | 23/253 R X |
| 3,227,523 | 1/1966 | Hoefker et al. | 23/253 R |
| 3,278,271 | 10/1966 | Kono et al. | 259/4 X |
| 3,285,712 | 11/1966 | Matasa et al. | 259/4 X |
| 3,294,490 | 12/1966 | Hach | 23/253 R |
| 3,567,389 | 3/1971 | Coulter et al. | 23/253 R |
| 3,607,071 | 9/1971 | Staffin et al. | 23/253 PC X |
| 3,645,142 | 2/1972 | Turpin | 23/259 X |
| 3,690,833 | 9/1972 | Ferrari | 23/253 R X |
| 3,764,268 | 10/1973 | Kosowsky et al. | 23/253 R |
| 3,773,423 | 11/1973 | Hach | 23/253 R X |
| 3,799,508 | 3/1974 | Arnold et al. | 259/4 |
| 3,800,219 | 3/1974 | Fosberg | 340/236 X |
| 3,846,075 | 11/1974 | Cioffi | 23/253 R |
| 3,904,365 | 9/1975 | Larson et al. | 23/253 R X |
| 3,905,902 | 9/1975 | Hoegberg et al. | 210/DIG. 25 |
| 3,916,674 | 11/1975 | Miller et al. | 73/61.1 R |

*Primary Examiner*—Joseph Scovronek
*Attorney, Agent, or Firm*—Pennie & Edmonds

[57] ABSTRACT

An automatic liquid analyzing apparatus for quantitatively measuring the parameter of a liquid is disclosed. The preferred embodiment of the invention comprises means for automatically and continuously obtaining a relatively pure sample of the liquid to be analyzed. Discrete quantities of the sampled liquid are reacted with discrete quantities of chemical reagents in accordance with the reaction which one desires to conduct. The transmittance of the reacted sample is then compared to the transmittance of the unreacted sample to obtain a measure of the parameter which one desires to monitor.

23 Claims, 15 Drawing Figures

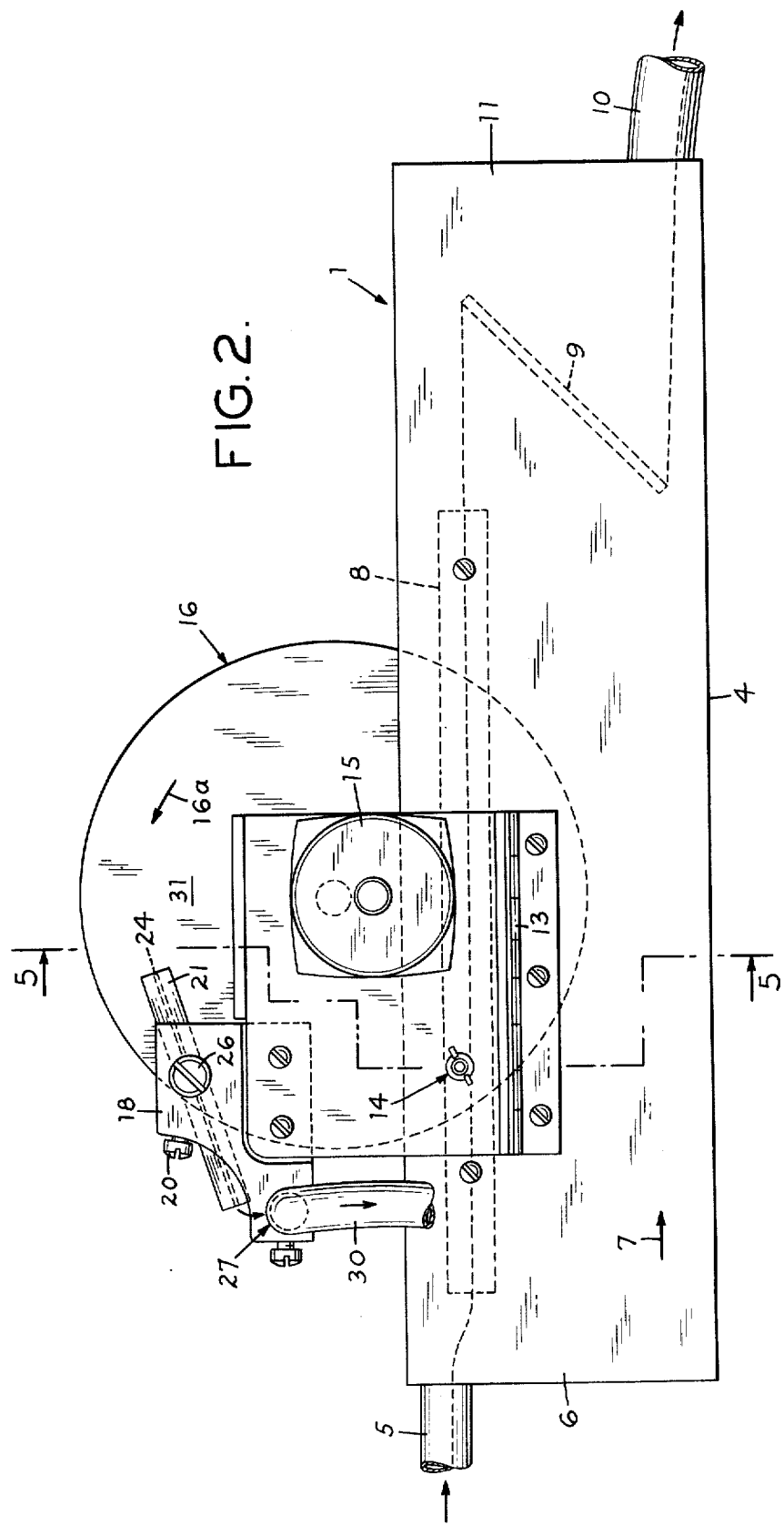

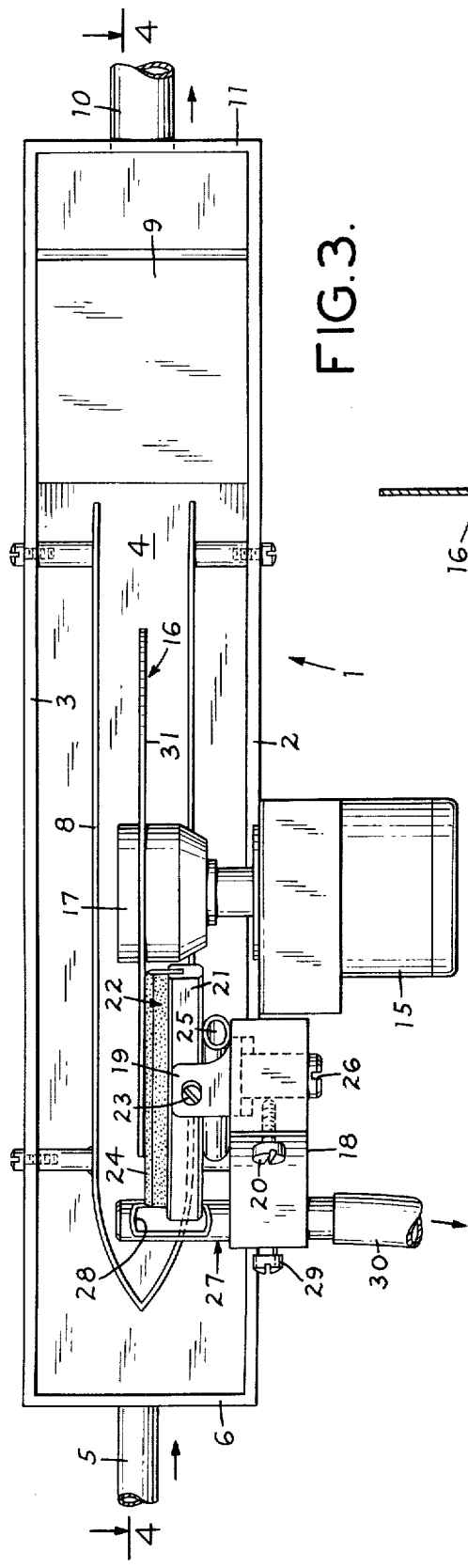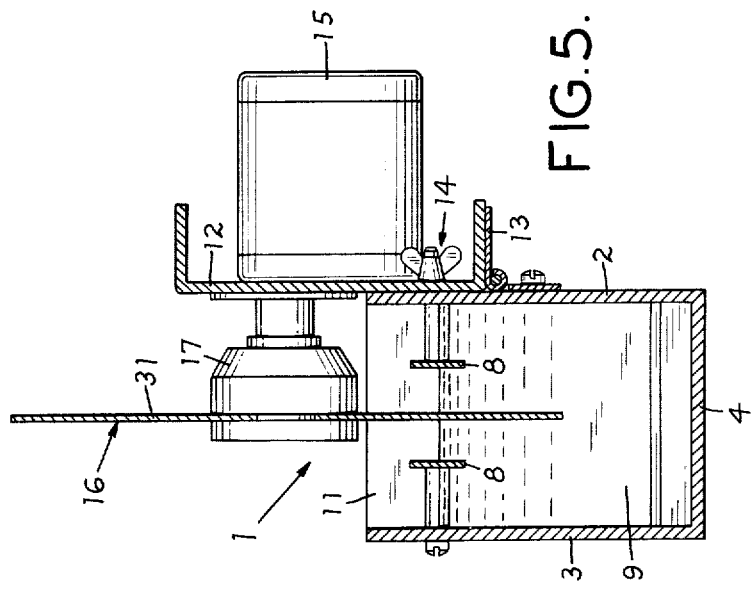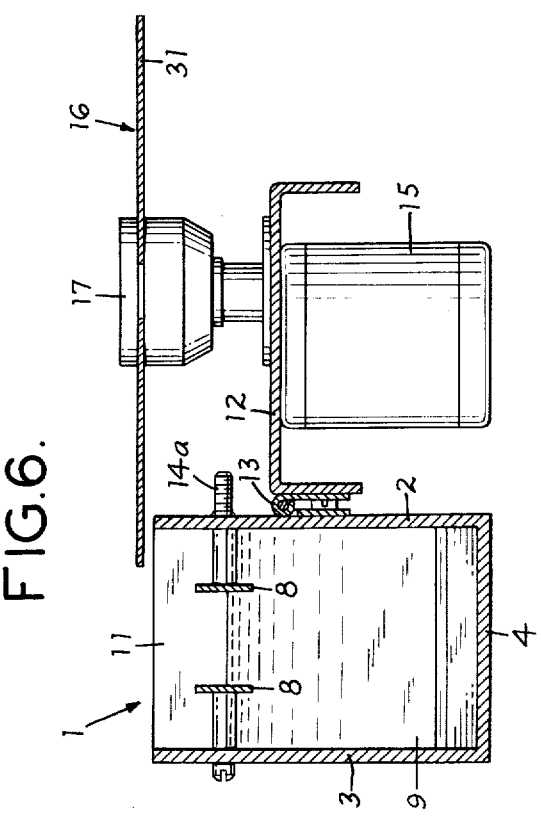

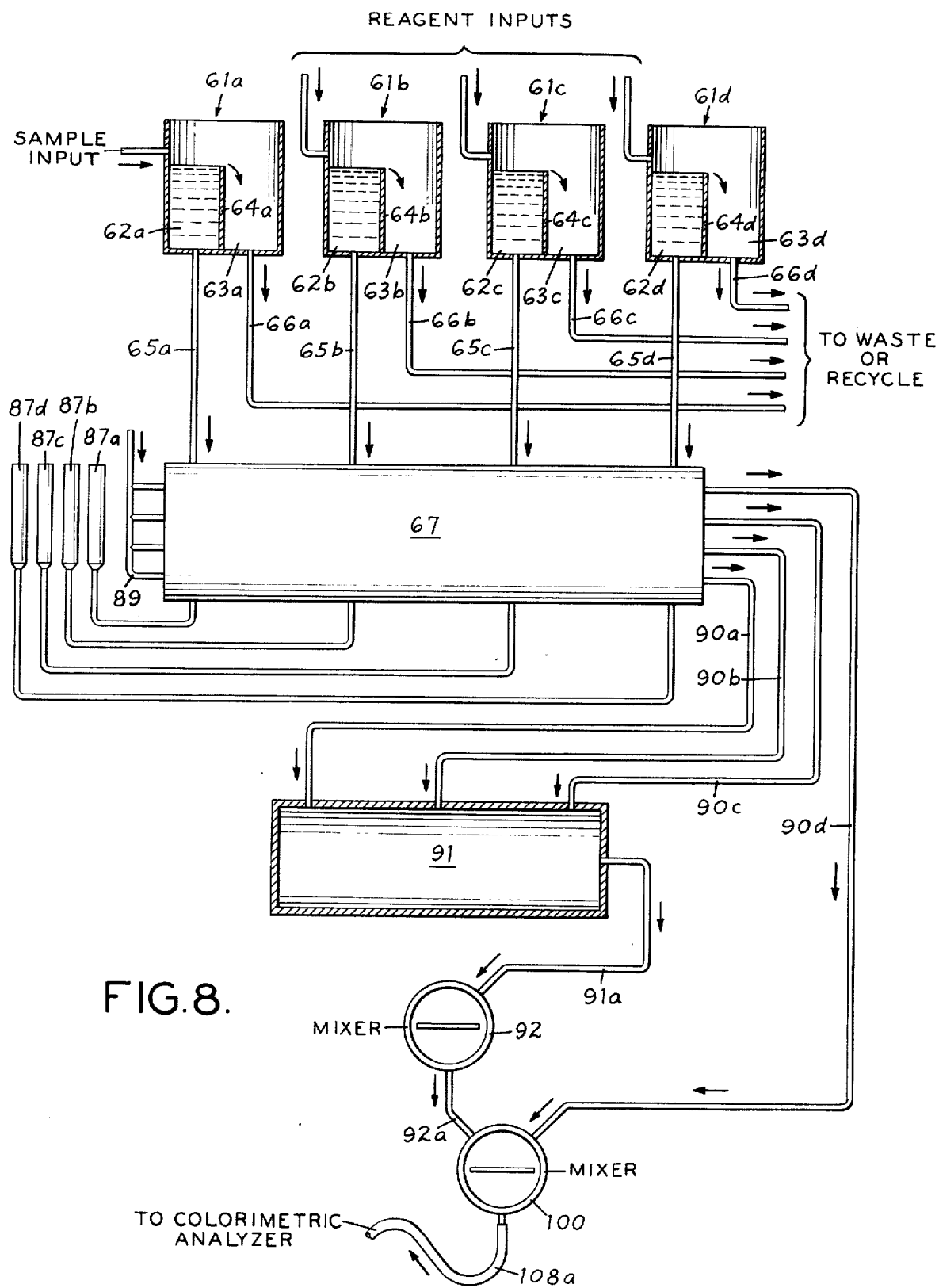

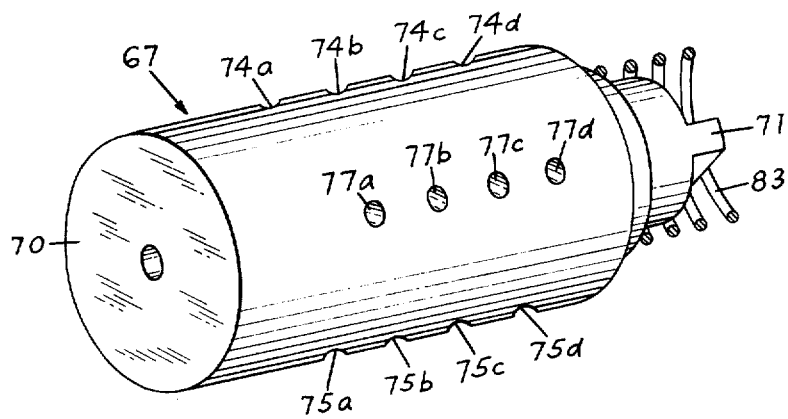
FIG.9.
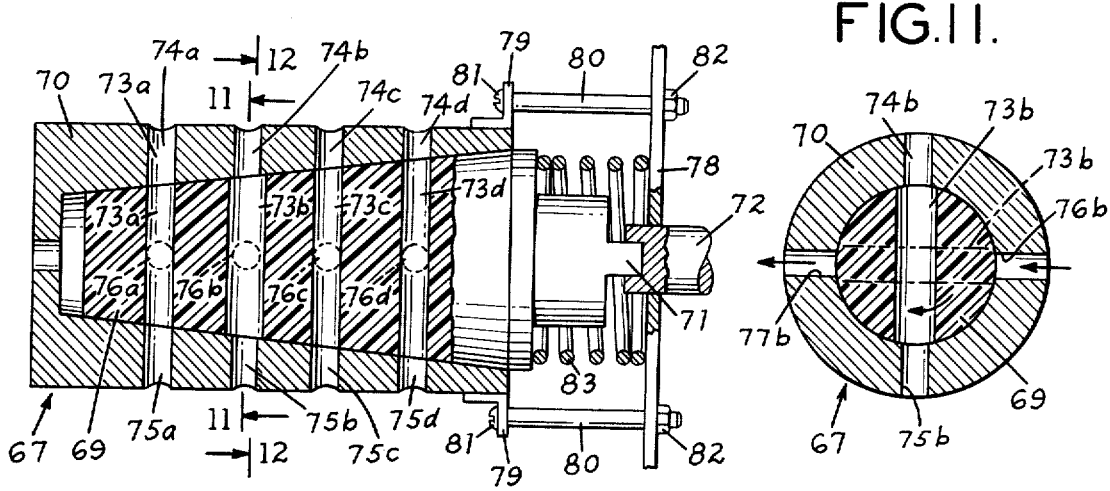
FIG.10.
FIG.11.
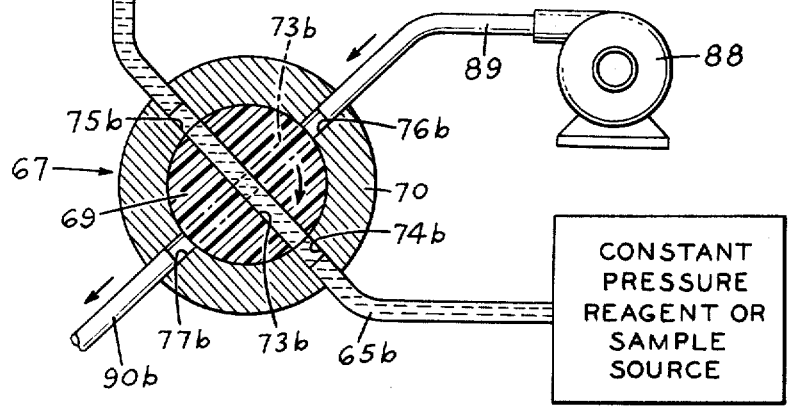
FIG.12.

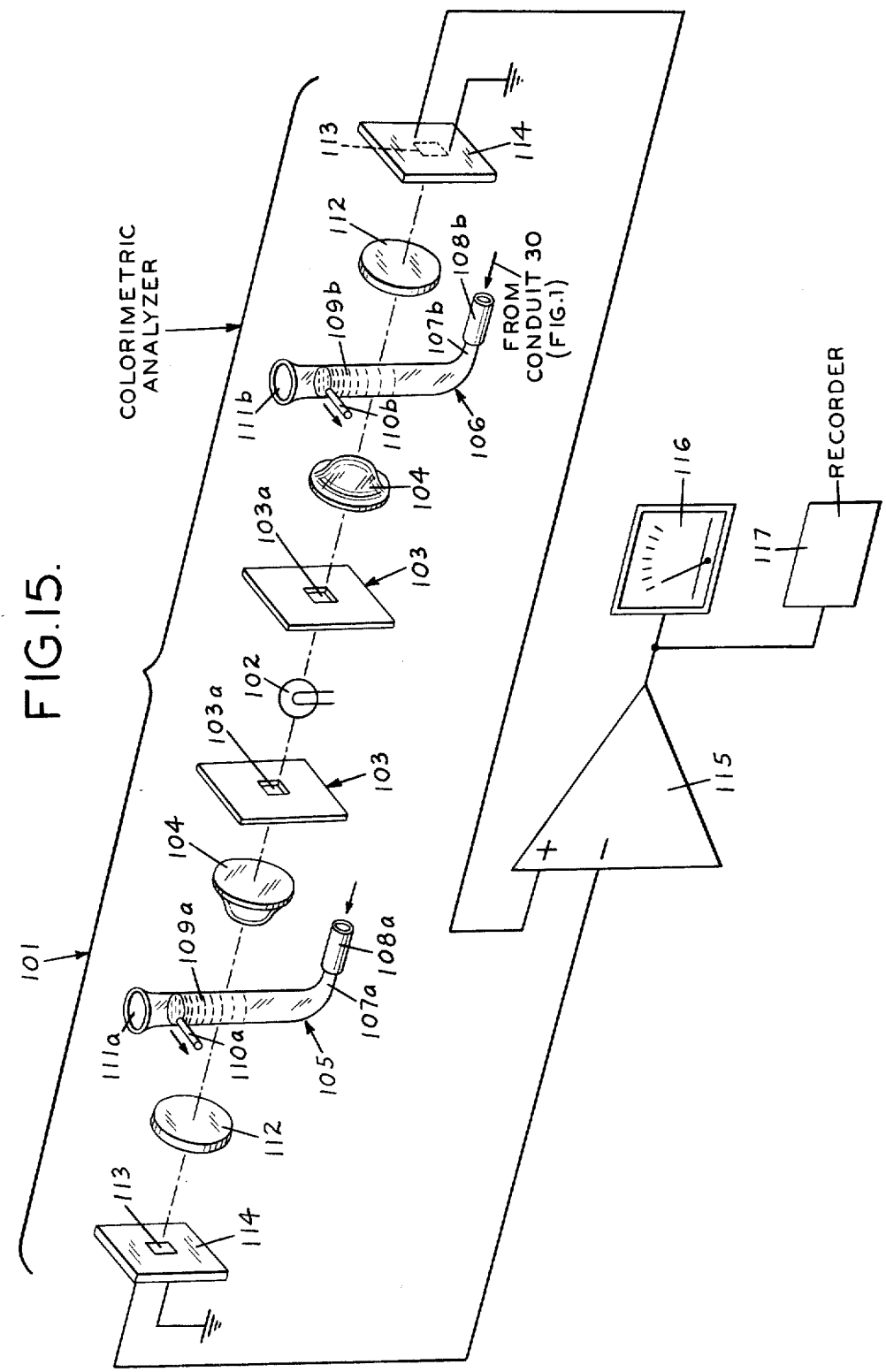

LIQUID ANALYSIS SYSTEM

BACKGROUND OF THE INVENTION

With increasing public concern over the quality of the environment, a significant need has arisen for equipment which is capable of accurately and economically testing various environmental conditions. The present invention, while suitable for employment in any situation requiring automated chemical analysis equipment, is particularly useful for continuously and automatically monitoring the quantity of pollutant in a body of water, such as a lake, stream or municipal water supply.

Conventionally, if one wishes to measure the level of pollutant, the biological oxygen demand or some other parameter of a body of water, one would take a sample of the water and submit it to an appropriate quantitative chemical analysis. These chemical tests generally comprise a number of steps involving the mixing and reacting of a predetermined amount of the sample or reacted sample with specific quantities of various chemical reagents.

These tests are best carried out individually by relatively highly skilled personnel. Naturally, of one wishes to use a test to obtain data continuously or at frequent intervals and thus construct an accurate and complete picture of the state of water quality over a period of time, conventional manual testing is quite expensive.

SUMMARY OF THE INVENTION

The present invention is directed toward an apparatus for obtaining a pure sample of a liquid to be tested and subjecting that sample to a quantitative chemical analysis. Such sampling, purification and quantitative analysis is performed automatically by the apparatus of the present invention. Results may be locally recorded and/or transmitted to a remote location. The apparatus of the present invention is particularly advantageous due to the relatively small amount of maintenance required and the compact, dependable and relatively simple nature of the apparatus.

The liquid sample is obtained by continuously submerging a surface in the liquid and collecting the thin liquid film which tends to adhere to that surface. In the preferred embodiment, a rotating disk is partially submerged in a trough through which a portion of the liquid to be sampled is continuously flowing. As the disk rotates in the liquid, the film of liquid that forms on its side surface is continuously removed by a blade which bears against the surface of the disk and sent via a tube to the analysis stages of the apparatus. Light particles are prevented from being taken up by the wheel through the provision of a deflector positioned upstream of the disk and partially submerged in the flowing liquid. Heavy particles such as sand are generally not caught by the wheel due to the fact that they tend to sink to the bottom of the trough. They are prevented from collecting there by the provision of a slit at the bottom of the trough downstream from the disk through which they are allowed to pass. In accordance with the present invention, the liquid sample thus obtained has been found to be of sufficient clarity and purity for most monitoring systems. However, under special circumstances, further purification and clarification may be advantageous.

For example, in some applications it may be desired to add a biocide to the sample to be tested. In this case, means are employed for measuring out predetermined quantities of sample liquid and combining that sample with a predetermined quantity of biocide. The sample and biocide may also be sent to a centrifuge which is used to remove any heavy particles which may be in the liquid sample.

If it is desired to use a centrifuge, the centrifuge is of the type which is periodically stopped and cleans itself by the vortex action of the swirling liquid inside it. When stopped, the liquid in the centrifuge continues turning and gradually exits in a vortex through holes which are at the bottom of the centrifuge, carrying the accumulated heavy particles through those holes and out of the centrifuge.

Analysis is performed on the sample liquid by combining predetermined quantities of the sample with one or a number of reagents in one or a number of reacting steps dependent upon the nature of the reaction which one wishes to conduct. In the preferred embodiment, the liquid and the reagents are sent to the analysis portion of the system under constant pressure to a metering device.

The metering device of the present invention facilitates the performance of water quality tests in an automated or semiautomated system by metering out accurately controlled quantities of testing reagents. Of course, the metering device of the present invention could also be advantageously employed in any apparatus requiring a highly precise metering operation.

In accordance with the present invention, metering is performed by a frustro-conical rotor which has a plurality of radially disposed bores along its length. The rotor is disposed in a housing whose inner surface mates with the frustro-conical shape of the rotor. The housing has first and second sets of radially disposed pairs of ports along its length. Each pair of ports of one of the sets is positioned in the housing in such a manner that each of the ports of a given port lines up with one of the ends of one of the bores when the rotor is in a given position. The other set of pairs of ports is aligned with the bores when the rotor is in a second position.

During operation, the rotor is rotated in the housing. One of each of the first set of pairs of ports is coupled to a source of reagent or the water to be tested. As the bores in the rotor become aligned with the first set of pairs of ports in the housing, liquid is caused to flow through one of each of the pairs of those ports, thereby filling the bores. Attached to the other port of each pair is a tube of sufficient height in relation to the pressure of the source as to receive the excess without overflow. As the rotor continues to rotate, the filled bores come into alignment with the second set of pairs of holes. One of the holes of each of the bores of this set is connected to a blower which, as the bores and the holes begin to align, blows the reagent that has filled the bores through the opposite hole of each bore which serves as an output.

The amount of reagent produced by the metering apparatus is a function of the volume of the bores in the rotor. It has been found desirable to feed the cone with a plurality of reagents and the sample which are provided to the metering device with the same pressure. This prevents migration of a reagent from one of the pairs of holes to another due to a difference in pressure head between the pairs. Although, in the described embodiment, all of the bores are filled and emptied simultaneously, the pattern can be varied by appropriate radial placement of the bores or ports to achieve any desired sequencing characteristics.

The output of the metering device is sent to an arrangement which may consist of blenders for combining the sample and reagents and mixing pots for thoroughly mixing the reagent chemicals, thereby insuring the completeness of the analysis reaction which one wishes to perform. The particular arrangement of blenders and mixing pots is dependent upon the particular steps which comprise the analysis reaction which one wishes to perform. There are a number of known prior art quantitative reactions for producing a reacted sample through the combination of the sample with a reagent or reagents in one or a number of steps. The thus produced reacted sample is then subjected to colorimetric analysis, or any other appropriate analytical technique.

BRIEF DESCRIPTION OF THE DRAWINGS

FIG. 2 is a side view of the preferred liquid sampling device shown in FIG. 1;

FIG. 3 is a plan view of the sampling device shown in FIG. 1;

FIG. 5 is a vertical section taken along line 5—5 of FIG. 2;

FIG. 6 is a figure similar to FIG. 5 showing the sampling disk in the retracted position rotated 90° for cleaning of the trough;

FIG. 8 is a flow diagram of an automatic analyzer constructed in accordance with the present invention;

FIG. 9 is a perspective view of the metering device utilized in the system illustrated in FIG. 8;

FIG. 10 is a view, partially in section, of the device illustrated in FIG. 9;

FIG. 11 is a cross-sectional view along line 11—11 of FIG. 10;

FIG. 12 is a cross-sectional view of the device illustrated in FIG. 9 along line 12—12 of FIG. 10 including a schematic illustration of the principle components of the system;

FIG. 15 is schematic exploded perspective view of a colorimetric analyzer to be used in conjunction with the system illustrated in FIG. 8.

DETAILED DESCRIPTION OF THE PREFERRED EMBODIMENT

Figure 1:
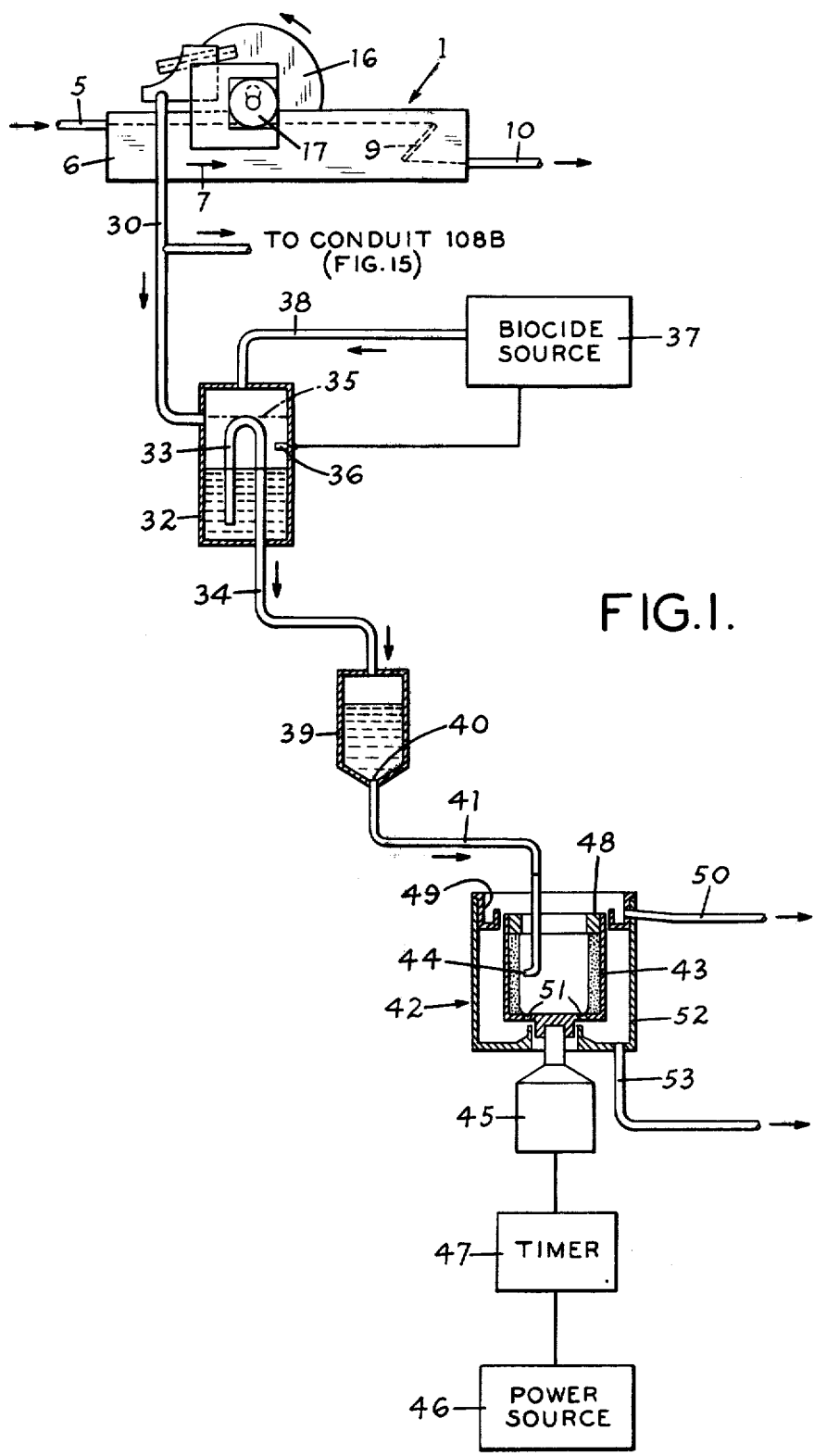
FIG. 1 is a flow diagram showing the sampling device with the optional purification and clarification system.
Figure 4:
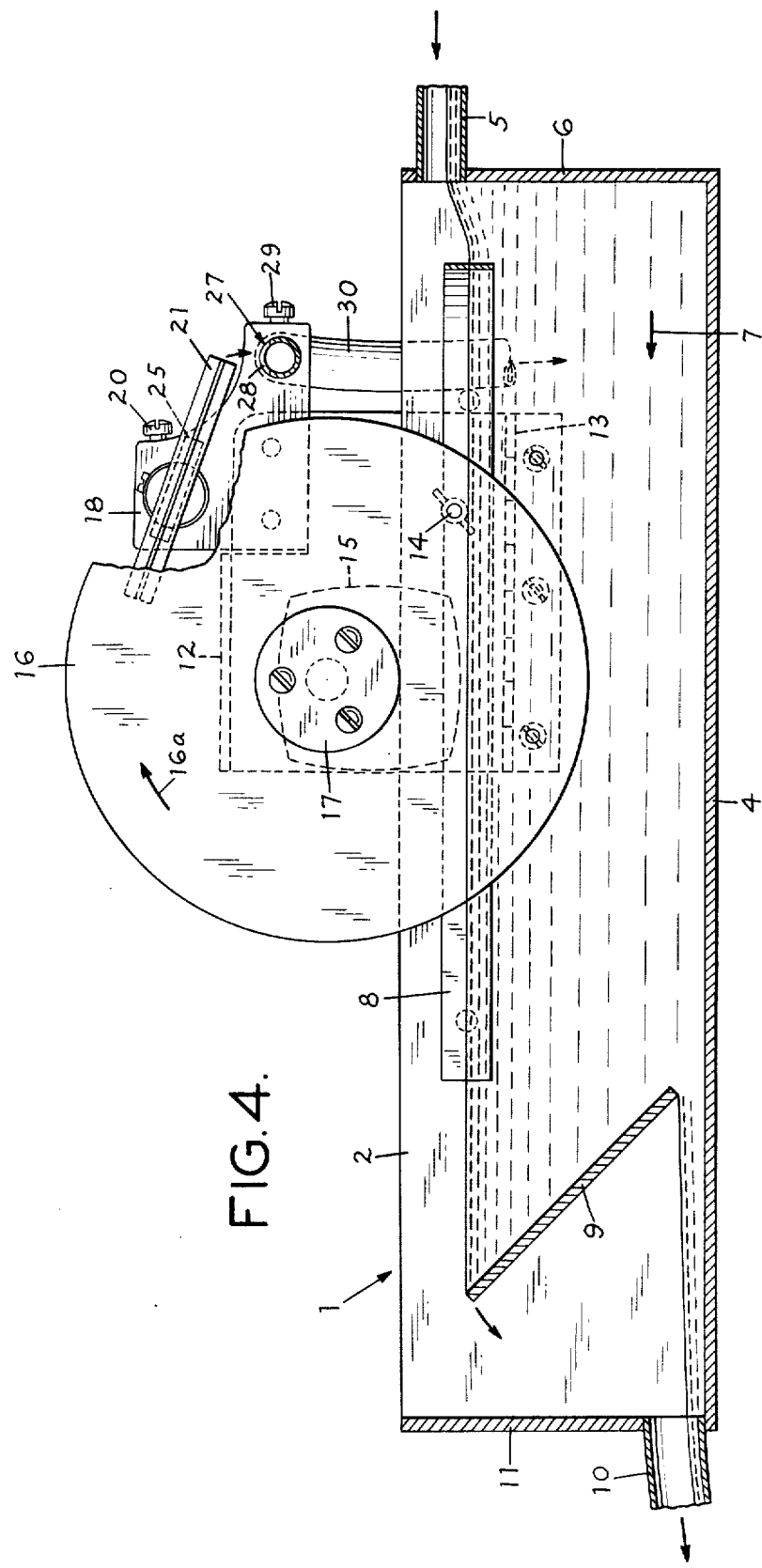
FIG. 4 is a longitudinal section taken along line 4—4 of FIG. 3.

Referring to FIG. 1, a portion of a liquid to be tested is caused to continuously flow through a sampling device 1. As illustrated in FIGS. 2–5, the sampling device 1 comprises a trough comprising a pair of sidewalls 2 and 3 secured to a bottom member 4. Liquid enters the trough through inlet conduit 5 in a front retaining wall 6 and travels through the trough in the direction indicated by arrow 7. Lighter particles which float on the surface of the liquid in the trough are deflected and thus prevented from entering the system by a baffle 8 secured to sidewalls 2 and 3. The lighter particles thus follow a path over a slanted rear wall 9. Heavier particles are carried along the bottom of the trough and exit through the aperture defined by slanted rear wall 9 and bottom member 4. An exit conduit 10 is mounted on a rear wall 11 for disposal of the liquid after it has passed through the sampling device.

The sampling mechanism is mounted on a support plate 12 which is secured to the sidewall 2 of the trough by a hinge 13 and bolt and wing-nut assembly 14. The bolt 14a is mounted in sidewall 2 of the trough. Removal of the wing-nut from the bolt allows the support plate to be pivotally displaced, (FIG. 6) thus permitting cleaning of the trough. A motor 15 is bolted to support plate 12. A disk 16 is mounted for rotation, in the direction indicated by arrow 16a, on the shaft of motor 15 through the use of a conventional mounting assembly 17. Also secured to support plate 12 is a sampling assembly support block 18. Mounted on support block 18 is a clevis 19 which is set at the desired position by a set screw 20. A wiper blade assembly comprising a support bar 21 and a conventional wiper blade 22, such as that used in an automobile, is secured to clevis 19 by a bolt 23. Insofar as it is desirable to have the wiping surface 24 of blade 22 just barely in contact with the surface of disk 16, a hole (not shown) drilled through support bar 21 through which bolt 23 passes is either somewhat larger in diameter than bolt 23 or elongated in shape. This allows the wiper blade assembly to be urged into the proper position by spring means 25 which may simply be a piece of flexible plastic tubing. Clevis 19 is also provided with an adjustment slot 26, which makes adjustment of the angular position of the clevis quite convenient.

Situated underneath the wiper blade assembly is a collection tube 27 having an opening 28 which is mounted in support block 18. The position of collection tube 27 is maintained by a set screw 29. Liquid collected in the collection tube is sent for analysis or further purification via a conduit 30.

In use, liquid proceeds through the trough in the direction indicated by arrow 7 in FIG. 1. Liquid accumulates in the trough and overflows rear wall 9. A small clearance is maintained between rear wall 9 and the bottom 4 of the trough, thus allowing heavy particles to exit below wall 9. Disk 16 rotates and its side surface 31 is thus coated with a thin film of the liquid. If the tangential velocities of submerged points on the disk's surface are less than the flow velocity through the trough, in some cases the likelihood of the disk's picking up impurities is reduced. The thin film is doctored from surface 31 by blade 22 which may be made or rubber or any other suitable material and is guided in collection tube 27 from which it proceeds via conduit 30 to the next stage. Floating particles are kept from reaching the disk by passing around baffle 8 and over the top of rear wall 9. Excess liquid passing both above and below rear wall 9 of the trough exits via conduit 10 from which it may be sent to a drain or returned to the body of liquid which is being sampled.

The liquid output of the sampling device is generally suitable for analysis and may be sent directly to the analyzing stages of the apparatus illustrated in FIGS. 8 and 15. However, in some situations, it may be desired to further purify and clarify the sampled liquid. In these cases, the sampled liquid is sent via conduit 30 to a vessel 32 (FIG. 1). Vessel 32 is a conventional siphoning device which is filled by conduit 3 and discharges its contents through siphon tube 33 and output conduit 34 when the level of sampled liquid exceeds the siphoning threshold. The threshold level 35 is the height of the top of siphoning tube 33. Prior to reaching the threshold level, at another level lower than the threshold a biocide is added to the sample. This other level may be sensed by a conventional level sensing switch 36. Level sensing switch 36 may be positioned to be actuated at any point before the tube is filled, thereby triggering biocide dispenser 37 to dispense a predetermined quantity of biocide into vessel 32 via conduit 38. This biocide would then mix with the liquid in the vessel and, when the level of liquid has exceeded the threshold of the siphoning device, a charge of sampled liquid and biocide will exit vessel 32 via conduit 34 under the action of gravity. Although pumps could be provided (for the purpose of saving space and the like), it is contemplated that the transfer of liquid from one stage to another in the apparatus is due to the effect of gravity.

The liquid leaving vessel 32 takes the form of a series of periodic discharges. However, because the remainder of the system is more advantageously operated when it is supplied with a continuous flow of liquid, a holding vessel 39 is provided. Holding vessel 39 is filled by conduit 34 and includes a small outlet 40 for slowly feeding liquid through a conduit 41 at a rate which is substantially independent of the periodic discharges through tube 34. The output of holding vessel 39 is sent via conduit 41 to a centrifuge 42 which may be made of plastic or any other suitable material. Centrifuge 42 includes a basket 43 and a feed nozzle 44 for feeding liquid into the basket. The centrifuge is rotated by a motor 45 which is ultimately powered by a power source 46. Power source 46 is controlled by a timing circuit 47. During operation of the centrifuge, basket 43 is rotated, causing filling of the periphery of the basket and separation of the lighter portion of the liquid which exits over the top surface element 48 of the basket into a collection trough 49 on the centrifuge. It then proceeds via conduit 50 to the next stage in the system. As the centrifuge is operated, heavy particles tend to collect on the inside of basket 43. In order to prevent accumulated impurities in the basket from impeding operation of the centrifuge, timer 47 periodically removes power from the motor rotating basket 43. The resulting vortex of liquid within the basket carries the liquid with the particles entrained in it through exit holes 51 on the bottom of the basket and into the outer casing 52 of the centrifuge. The liquid with the impurities entrained in it then exits through a waste conduit 53.

Figure 7:
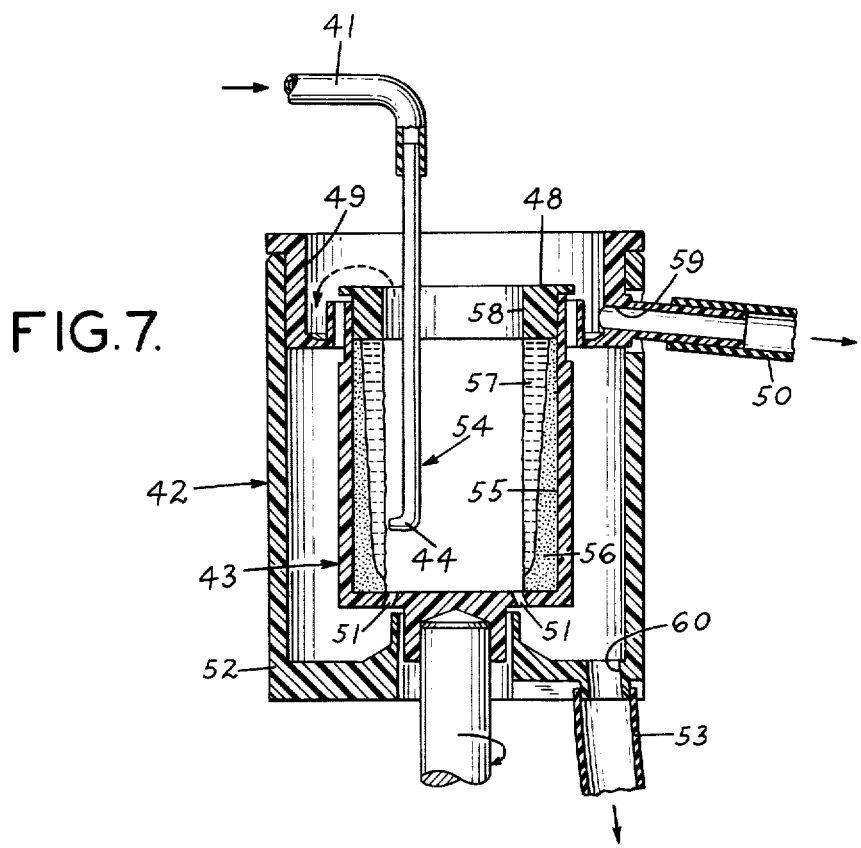
FIG. 7 is a cross-sectional view of the preferred centrifuge shown in FIG. 1.

A cross-sectional view of the preferred centrifuge is illustrated in FIG. 7. The centrifuge comprises outer casing 52 which contains basket 43 which is rotated at a relatively high speed within the casing by the motor. Liquid is fed into the centrifuge by a feed tube 54 from which it exits through nozzle 44. The liquid thus forms on the sidewalls 55 of the basket. As the liquid rises along the sidewalls, the heavier particles 56 tend to separate from the clear liquid 57, thus effecting substantially complete separation before the liquid reaches the top of the basket. As liquid is continually added by nozzle 44, the clear liquid overflows an annular element 58. Due to the centrifugal action of the basket, the clear liquid is then projected from the basket into collection trough 49 through which it exits via an outlet port 59.

As discussed above, the motor is periodically stopped. This results in a swirling vortex of liquid within the basket 43, causing the liquid and the particles inside the basket to be carried through exit holes 51 into the casing 52 of the centrifuge. The particles then leave via drain port 60 and conduit 53.

Referring to FIG. 8, a portion of the sampled liquid either from the centrifuge or directly from the sampling device 1 is sent to constant pressure liquid source 61a. A set of constant pressure sources 61a–d comprises a plurality of sources corresponding to the sample liquid to be tested and the reagents to be used in the reaction. Each constant pressure source is divided into two cells 62a–d. Liquid from the sample source and the other reagent sources enters cells 62a–d and fills each to the top of center dividers 64a–d. The tops of all the center dividers are at the same level. Hence, the pressure at the bottom of each of the cells 62a–d is uniform, as a consequence of the fact that each of the output conduits sees the same height of liquid above it. This results in a constant pressure at the output of conduits 65a–d which are of uniform height leading from constant pressure source 61. Overflow from cells 62a–d is received into cells 63a–d and exits through drain conduits 66a–d. The drained portion of the sample or reagents may either be wasted or recycled. The output conduits 65a–d are coupled to metering unit 67.

As illustrated in FIGS. 9–11, the metering device 67 of the present invention comprises a tapered rotor 69 in a housing 70. Rotor 69 includes an extension 71 to which a source of motive power such as motor shaft 72 is coupled, thus allowing the rotor to be rotated. A plurality of bores 73a–d are disposed in rotor 69. The volume of the bores is chosen to be equal to the quantity of liquid which one wishes to meter out. The device 67 is positioned so that the average height of each bore is the same distance below the output ports of the constant pressure sources 61a–d. As can be seen most clearly in FIG. 11, each bore 73a–d, when rotor 69 is in the proper angular position with respect to housing 70, lines up with its corresponding reagent feeding ports 74a–d which are coupled to conduits 65a–d, respectively, and reagent overflow ports 75a–d. As shown in phantom lines in FIG. 11, at a second angular position, bores 73a–d are in alignment with pressure ports 76a–d and reagent output ports 77a–d.

Housing 70 may be supported on any surface 78 of the apparatus in which it is to be used. A typical support may comprise a number of brackets 79 secured to the outer periphery of the housing and supported on surface 78 by a corresponding number of sleeves 80 which are secured to the brackets and surface 78 by bolts 81 and nuts 82.

The use of a tapered rotor and housing is particularly advantageous due to the fact that such a configuration does not require very precise machining during manufacture. It is also noted that the rotor may be made of a plastic material such as Teflon which is softer than the housing and which, with use, tends to conform in shape to the shape of the inside mating surface of the housing and thus minimize leakage. Leakage can be effectively eliminated by using a spring 83 to urge the rotor into the housing.

The angle of the taper in the frustro-conical rotor has also been found to be important. Specifically, if the taper is relatively shallow, jamming tends to occur as the spring urges the rotor into the housing. If, on the other hand, the taper is made too steep, leakage becomes a problem, and an extremely strong spring is needed to prevent leakage. In practice, it has been found that a taper of approximately 6° from the axis of rotation functions quite satisfactorily for most applications, although any angle in the range between 2° and 10° will work with varying degrees of success.

The operation of the metering device illustrated in FIGS. 9-11 is schematically illustrated in FIG. 12. For simplicity of illustration, only the connections associated with a single bore 73b have been shown. The system includes a plurality of conduits 65a–d which receive reagent from one of the constant pressure source cells 62a–d which feed the sample and a plurality of reagents to the metering device 67. Each of the reagents is fed to the metering device with the same pressure in order that the migration of reagents between the input ports 74a–d at the interface between rotor 69 and housing 70 is minimized.

Each source cell 62a–d thus feeds a reagent or sample into its corresponding bore 73a–d through a corresponding reagent feeding port 74a–d. Due to the nature of the arrangement, such feeding is made with relatively little turbulence, thereby achieving a high degree of uniformity in the filling operation. During filling, after the reagent or liquid has filled the bore, it proceeds through overflow ports 75a–d and into overflow tubes 87a–d. The volume of reagent liquid in bores 73a–d is, therefore, equal to the volume of the bore. Overflow tubes 87a–d are also filled with liquid to a height dependent upon the pressure with which the liquid reagent is fed to the metering device 67.

As the rotor 69 continues to turn with respect to the housing 70, it comes to the position shown in phantom lines in FIG. 12. In this position, a blower 88 (FIG. 12) blows air through a conduit 89 to pressure ports 76a–d, thereby driving the volume of reagent in bores 73a–d through output ports 77a–d and output conduits 90a–d. In this manner, predetermined discrete volumes of liquid reagent or liquid to be tested are metered out in discrete fashion. Naturally, if one desired to do so, one could vary the sequence of feeding by variation of the position of the bores and ports.

Figure 13:
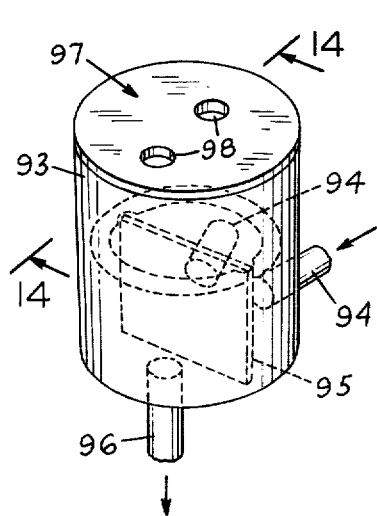
FIG. 13 is a perspective view of a mixer of the type used in the system illutrated in FIG. 8.
Figure 14:
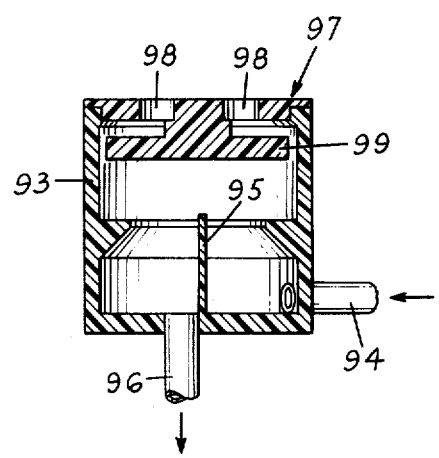
FIG. 14 is a cross-sectional view along line 14—14 of FIG. 13.

The output of the metering device may then be sent to any combination of blenders and mixers which would be appropriate for carrying out the quantitative analysis which one wishes to perform. By way of example, the metering device, which has four outputs supplying discrete and predetermined amounts of three reagents and a sample may be connected as shown in FIG. 8. In this particular arrangement, the sample to be tested and two reagents are sent to a blender 91 which is merely a chamber with a plurality of inputs and a single output. The output of the blender is sent via a conduit 91a to a first mixing pot 92 of the type illustrated in FIGS. 13 and 14. The mixing pot comprises a housing 93 with inlets 94. Liquid entering an inlet port is dashed against divider wall 95 in the casing, causing a thorough mixing action. The liquid thus fills that volume of the casing in communication with the inlets with a thoroughly mixed liquid which is caused to overflow beyond divider wall 95 into that volume of the mixing pot in communication with an outlet 96. Proper venting is insured by a cap 97 which has venting ports 98 disposed in it. The cap also prevents splashing of the liquid outside the mixing pot by the provision of a disk-shaped baffle portion 99. The diameter of barrier 99 is less than the inside diameter of housing 93, thus allowing communication with venting port 98.

In accordance with the embodiment shown in FIG. 8, the output of mixing pot 92 is then sent via conduit 92a to a second mixing pot 100 along with the third reagent output of the metering device. These two liquids are then combined in second mixing pot 100 and sent to a colorimetric analyzer.

A colorimetric analyzer 101 particularly useful in conjunction with the apparatus of the present invention is illustrated in exploded perspective in FIG. 15. Light is supplied by a conventional incandescent lamps 102. The source is shielded by a pair of opaque masks 103 with apertures 103a and focused by a pair of bullseye lenses 104. The images of the apertures 103a are focused through a pair of liquid-containing tubes 105 and 106. Tube 105 is fed with the continuously flowing reacted output of mixing pot 100. Tube 106 is fed with a portion of the continuously flowing output of the sample source which also feeds the input of constant pressure source 61a. The construction of the tubes is shown in FIG. 15 and comprises input portions 107a–b to which input tubes 108a–b are coupled. Liquid flows up through body portions 109a–b of the tubes overflowing through outlet ports 110a–b. Proper venting is provided by open ends 111a–b at the top of the tube.

It may also be desirable to pass the light which has passed through the sample liquid contained in tubes 105 and 106 through an appropriate pair of filters 112 before the light forms images of the apertures on photocells 114. Naturally, the intensity of images 113 is a function of the transmittance of the filters and the liquid in the vials. Due to the nature of the reaction carried out on the sampled liquid, the transmittance of the reacted sample is related to the parameter which one wishes to measure. The difference between the intensity of light transmitted through the unreacted sample and the reacted sample is thus a measure of the desired parameter. Each of the photocells produce an electrical signal which is proportional to the intensity of the image incident on its face. The signals from the photocells are then sent to a differential amplifier 115 which produces at its output an electrical signal indicative of the difference in intensities. This signal may be used to drive one or a plurality of indicating or recording devices such as meter 116 or recorder 117 for providing a continuous display and permanent record of the parameter which one wishes to measure.

We claim:
1. An automatic liquid analysis apparatus for quantitatively measuring a parameter of a liquid, comprising:
   a. constant pressure supply means for providing a sample of the liquid to be analyzed and at least one reagent at a substantially equal constant pressure;
   b. a metering device for separately receiving said sample and said reagent and separately dispensing said sample and said reagent in a periodic series of discrete charges of predetermined magnitude, said metering device including:
      i. a housing having inner and outer walls,
      ii. a plurality of input ports in said housing, each of which is coupled from the outer wall thereof to one of the constant pressure supply means,
      iii. a plurality of output ports in said housing, each of which is spaced from said input ports and coupled from the outer wall thereof to said mixing means,
      iv. a valve member movably received within said housing and having an outer wall disposed in engagement with the inner wall of said housing;
      v. a plurality of conduit chambers extending through said valve member, one chamber for each of the input-output means in said housing, and vi. said valve member being movable within said housing from a first position wherein each of said chambers is in communication with one of the input means in said housing and a second position wherein each of said chambers is in communication with one of the output means in said housing;

c. mixing means for mixing and reacting the discrete charges of reagent and sample to produce a reacted sample; and d. means for analyzing said reacted sample to determine the parameter which one wishes to measure.

2. Apparatus as in claim 1, wherein said means for analyzing said reacted sample is a colorimetric analyzer comprising:
 a. first vessel means for containing said reacted sample;
 b. second vessel means for containing a portion of the unreacted sample;
 c. a single light source disposed between and passing light through said first vessel means and said second vessel means;
 d. first photo sensitive means for receiving light from said light source which has been passed through said first vessel means;
 e. second photo sensitive means for receiving light from said light source which has been passed through said second vessel means; and
 f. means responsive to said first and second photo sensitive means to produce a signal proportional to the parameter which one wishes to measure.

3. Apparatus as in claim 1, wherein said means for providing a sample of the liquid comprises:
 a. a member having a flat planar fluid wettable surface;
 b. means for alternately and periodically submerging a first portion of said surface in the liquid to be tested while withdrawing a second portion of said surface from said liquid, and submerging said second portion while withdrawing said first portion from the liquid, causing the formation of a thin film of said liquid on the withdrawn portion of said surface; and
 c. means for removing said thin film from the portion of said surface that has been withdrawn from said liquid before that portion is again submerged to obtain a sample of said liquid.

4. Apparatus as in claim 3, wherein said means for alternately submerging and withdrawing said surface is a motor for rotating said member.

5. Apparatus as in claim 4, wherein said member is a disk.

6. Apparatus as in claim 4, wherein said means for removing said thin film is a blade which bears against said surface.

7. Apparatus as in claim 3, further comprising a trough for receiving a portion of the liquid to be sampled, said member having a surface, said means for alternately submerging and withdrawing said surface, and said means for removing said thin film being supported on said trough.

8. Apparatus as in claim 1, wherein said means for providing a sample of the liquid to be analyzed and at least one reagent at an equal constant pressure comprises a plurality of chambers each having at least one cell defined by a divider wall, said divider wall positioned, configured and dimensioned in such a manner that overflow from said cell is caused to pass over the top of said divider wall, means for introducing a liquid into each of said cells, and output port means connected to each of said first cells for supplying liquid to said metering device, the tops of each of said divider walls being at substantially equal heights above said metering device.

9. A mixer for mixing and reacting fluids, comprising:
 a. a housing having at least one input port and one output port;
 b. a dividing wall separating said housing into first and second chambers, said first chamber in communication with said input port and said second chamber in communication with said output port, said dividing wall extending from the bottom of said housing but terminating at a level below the upper end of said housing, whereby liquid is caused to enter said first chamber through said input port, fill said first chamber, overflow into said second chamber and exit via said output port;
 c. cap means defining at least one venting hole disposed over the open end of said housing; and
 d. baffle means disposed under said cap means and secured to said cap means for preventing the direct expulsion of fluid through said venting hole and allowing pneumatic communication between said venting holes and said first and second chambers, said baffle means having a planar cross-sectional area less than the inner cross-sectional area of said housing.

10. An automatic liquid analysis apparatus for quantitatively measuring a parameter of a liquid, comprising:
 a. means for providing a sample of the liquid to be analyzed and at least one reagent at a substantially equal constant pressure, said means comprising:
  i. a member having a flat planar fluid wettable surface,
  ii. means for alternately and periodically submerging a first portion of said surface in the liquid to be tested while withdrawing a second portion of said surface from said liquid, and submerging said second portion while withdrawing said first portion from the liquid, causing the formation of a thin film of said liquid on the withdrawn portion of said surface,
  iii. means for removing said thin film from the portion of said surface that has been withdrawn from said liquid before that portion is again submerged to obtain a sample of said liquid, and
  iv. baffle means disposed partially submerged beneath the surface of said liquid upstream of said member for deflecting particles floating on the surface of said liquid away from said surface;
 b. a metering device for separately receiving said sample and said reagent and separately dispensing said sample and said reagent in a periodic series of discrete charges of predetermined magnitude;
 c. means for mixing and reacting the discrete charges of reagent and sample to produce a reacted sample; and
 d. means for analyzing said reacted sample to determine the parameter which one wishes to measure.

11. An automatic liquid analysis apparatus for quantitatively measuring a parameter of a liquid, comprising:

a. means for providing a sample of the liquid to be analyzed and at least one reagent at a substantially equal constant pressure, said means comprising:
   i. a member having a flat planar fluid wettable surface,
   ii. means for alternately and periodically submerging a first portion of said surface in the liquid to be tested while withdrawing a second portion of said surface from said liquid, and submerging said second portion while withdrawing said first portion from the liquid, causing the formation of a thin film of said liquid on the withdrawn portion of said surface,
   iii. means for removing said thin film from the portion of said surface that has been withdrawn from said liquid before that portion is again submerged to obtain a sample of said liquid, and
   iv. a trough for receiving a portion of the liquid to be sampled, said trough including a a wall downstream from said member and extending transversely to the direction of flow through said trough, said wall being spaced from the bottom of the trough whereby heavy particles accumulating at the bottom of said trough are caused to flow from said trough between the bottom of said trough and said wall;
b. a metering device for separately receiving said sample and said reagent and separately dispensing said sample and said reagent in a periodic series of discrete charges of predetermined magnitude;
c. means for mixing and reacting the discrete charges of reagent and sample to produce a reacted sample; and
d. means for analyzing said reacted sample to determine the parameter which one wishes to measure.

12. Apparatus as in claim 11, wherein said means for alternately submerging and withdrawing said surface is a motor for rotating said planar surface.

13. Apparatus as in claim 12, wherein said means for removing said thin film is a blade which bears against said surface.

14. Apparatus as in claim 11, further comprising baffle means disposed partially submerged beneath the surface of said liquid for deflecting particles floating on the surface of said liquid away from said surface.

15. An automatic liquid analysis apparatus for quantitatively measuring a parameter of a liquid, comprising:
a. means for providing a sample of the liquid to be analyzed and at least one reagent at a substantially equal constant pressure, said means comprising:
   i. a member having a flat planar fluid wettable surface,
   ii. means for alternately and periodically submerging a first portion of said surface in the liquid to be tested while withdrawing a second portion of said surface from said liquid, and submerging said second portion while withdrawing said first portion from the liquid, causing the formation of a thin film of said liquid on the withdrawn portion of said surface,
   iii. means for removing said thin film from the portion of said surface that has been withdrawn from said liquid before that portion is again submerged to obtain a sample of said liquid,
   iv. siphon means for measuring out discrete predetermined volumes of said sample;
   v. means for adding a predetermined amount of biocide to each of said discrete volumes of liquid, and
   vi. centrifuge means for removing impurities from said liquid to which biocide has been added;
b. a metering device for separately receiving said sample of said reagent and separately dispensing said sample and said reagent in a periodic series of discrete charges of predetermined magnitude;
c. means for mixing and reacting the discrete charges of reagent and sample to produce a reacted sample; and
d. means for analyzing said reacted sample to determine the parameter which one wishes to measure.

16. An automatic liquid analysis apparatus for quantitatively measuring a parameter of a liquid, comprising:
a. means for providing a sample of the liquid to be analyzed and at least one reagent at a substantially equal constant pressure;
b. a metering device for separately receiving said sample and said reagent and separately dispensing said sample and said reagent in a periodic series of discrete charges of predetermined magnitude;
c. means for mixing and reacting the discrete charges of reagent and sample to produce a reacted sample;
d. means for analyzing said reacted sample to determine the parameter which one wishes to measure; and
e. said mixing means for reacting said discrete charges to produce a reacted sample comprises at least one mixing vessel comprising:
   i. a housing having at least one input port and one output port,
   ii. a dividing wall separating said housing into first and second chambers, said first chamber in communication with said input port and said second chamber in communication with said output port, said dividing wall extending from the bottom of said housing but terminating at a level below the upper end of said housing, whereby liquid is caused to enter said first chamber through said input port, fill said first chamber, overflow into said second chamber and exit via said output port,
   iii. cap means defining at least one venting hole disposed over the open end of said housing, and
   iv. baffle means disposed under said cap means and secured to said cap means for preventing the direct expulsion of fluid through said venting hole and allowing pneumatic communication between said venting holes and said first and second chambers, said baffle means having a planar cross-sectional area less than the inner cross-sectional area of said housing.

17. An automatic liquid analysis apparatus for quantitatively measuring a parameter of a liquid, comprising:
a. means for providing a sample of the liquid to be analyzed and at least one reagent at a substantially equal constant pressure; and
b. a metering device for separately receiving said sample and said reagent and separately dispensing said sample and said reagent in a periodic series of discrete charges of predetermined magnitude, said metering device comprising:
   i. a rotor having a plurality of chambers, each of said chambers having first and second openings, ii. a housing for receiving said rotor, said housing having:
1. a plurality of corresponding input ports coupled to the constant pressure supply, each communicating with one opening in its corresponding chamber when said rotor is in a first angular position with respect to said housing,
2. a plurality of corresponding overflow ports, each communicating with the other opening of its corresponding chamber when its corresponding input port is in communication with said one opening of its corresponding chamber,
3. a plurality of corresponding pressure ports, each communicating with one opening in its corresponding chamber when said rotor is in a second angular position with respect to said housing, and
4. a plurality of corresponding output ports coupled to said analyzing means, each communicating with one opening of its corresponding chamber when its corresponding pressure port is in communication with said one opening of its corresponding chamber,
iii. overflow receiving means connected to said overflow ports, and
iv. means for applying pressure to said plurality of pressure ports.

18. Apparatus as in claim 17, wherein said rotor has a conical shape and said housing has a mating conical surface.

19. Apparatus as set forth in claim 18, wherein each of said chambers is a bore which extends radially through said rotor.

20. Apparatus as in claim 19, further comprising a spring for urging said rotor into said housing.

21. Apparatus as in claim 19, wherein said rotor is made of a material which is softer than the material of which said housing is made.

22. A device as in claim 21, wherein said material is Teflon.

23. Apparatus as in claim 17, wherein the rotor is conical in shape and has an outer surface that diverges from the axis of rotation of the cone by an angle within the range of 2° to 10°.

* * * * *

UNITED STATES PATENT AND TRADEMARK OFFICE
CERTIFICATE OF CORRECTION

PATENT NO. : 3,999,945
DATED : December 28, 1976
INVENTOR(S) : Jack Kushner and Henry G. Zwirblis It is certified that error appears in the above-identified patent and that said Letters Patent are hereby corrected as shown below:

Column 1, line 25, "of" should read --if--.

Column 2, line 38, "port lines" should read --port pair lines--.

Column 3, line 48, "illutrated" should read --illustrated--.

Column 4, line 66, "conduit 3" should read --conduit 30--.

Column 6, line 12, "62a-d." should read --62a-d and 63a-d.--.

Column 7, line 66, "port" should read --ports--.

Column 11, line 19, "a a wall" should read --a wall--.

Signed and Sealed this

Twenty-sixth Day of April 1977

[SEAL]

Attest:

RUTH C. MASON
Attesting Officer

C. MARSHALL DANN
Commissioner of Patents and Trademarks